United States Patent
Key et al.

(10) Patent No.: US 10,281,374 B2
(45) Date of Patent: May 7, 2019

(54) METHOD OF PRETREATMENT OF BIOLOGICAL SAMPLES FOR AN ANALYTE-STAINING ASSAY METHOD

(71) Applicants: Marc Key, Ojai, CA (US); Bipin Gupta, Pleasanton, CA (US)

(72) Inventors: Marc Key, Ojai, CA (US); Bipin Gupta, Pleasanton, CA (US)

(73) Assignees: Diagnostic BioSystems, Pleasanton, CA (US); Marc Key, Ojai, CA (US)

( * ) Notice: Subject to any disclaimer, the term of this patent is extended or adjusted under 35 U.S.C. 154(b) by 207 days.

(21) Appl. No.: 15/256,609

(22) Filed: Sep. 4, 2016

(65) Prior Publication Data

US 2017/0122850 A1  May 4, 2017

Related U.S. Application Data

(60) Provisional application No. 62/250,727, filed on Nov. 4, 2015.

(51) Int. Cl.
```
C12Q 1/68      (2018.01)
G01N 33/53     (2006.01)
C07H 21/00     (2006.01)
G01N 1/30      (2006.01)
G01N 1/34      (2006.01)
G01N 1/44      (2006.01)
C12N 9/54      (2006.01)
```
(52) U.S. Cl.
CPC ............. *G01N 1/30* (2013.01); *C12N 9/54* (2013.01); *G01N 1/34* (2013.01); *G01N 1/44* (2013.01)

(58) Field of Classification Search
CPC .................................. C12Q 1/68; G01N 33/53
See application file for complete search history.

(56) References Cited

U.S. PATENT DOCUMENTS

| | | | | |
|---|---|---|---|---|
| 1,999,341 | A * | 4/1935 | Muth et al. | C07D 209/88 548/440 |
| 4,442,214 | A * | 4/1984 | Morgan | C12N 9/52 435/219 |
| 5,242,817 | A * | 9/1993 | Kelly | C12N 9/52 435/212 |
| 5,393,772 | A * | 2/1995 | Yue | A61K 31/40 514/410 |
| 5,405,863 | A * | 4/1995 | Barone | A61K 31/40 514/411 |
| 2004/0001842 | A1 * | 1/2004 | Michaeli | A61K 39/0005 424/185.1 |
| 2006/0040341 | A1 * | 2/2006 | Bland | B01L 3/545 435/40.5 |
| 2012/0028298 | A1 * | 2/2012 | Takayama | G01N 1/312 435/40.52 |
| 2013/0189730 | A1 * | 7/2013 | Freeland | G01N 1/30 435/40.52 |
| 2014/0017749 | A1 * | 1/2014 | Deinhammer | C12Y 302/01001 435/161 |
| 2014/0051118 | A1 * | 2/2014 | Matthiesen | G01N 1/30 435/40.5 |
| 2014/0147838 | A1 * | 5/2014 | Sempere | C12Q 1/6841 435/6.11 |
| 2014/0273088 | A1 * | 9/2014 | Winther | G01N 1/312 435/40.52 |
| 2015/0037802 | A1 * | 2/2015 | Wang | C25D 1/006 435/6.12 |
| 2015/0216664 | A1 * | 8/2015 | Ingham | A61L 27/3608 623/23.63 |
| 2017/0183740 | A1 * | 6/2017 | Yu | C12Q 1/6886 |
| 2018/0147166 | A1 * | 5/2018 | Dong | A61K 31/166 |
| 2018/0164321 | A1 * | 6/2018 | Wang | C07K 16/2878 |
| 2018/0290306 | A1 * | 10/2018 | Elliot | B01L 3/545 |

OTHER PUBLICATIONS

Brianlou et al. Development b106:611 (Year: 1989).*
Butler et al. Methods 23: 303 (Year: 2001).*
Newton et al., Brain Research Protocols 9 : 214 (Year: 2002).*
Naranjanakumari et al. Methods 26:182 (Year: 2002).*
Ramos-Vara, Vet Pathology 42: 405 (Year: 2005).*
Shi et al. J. of Histochemistry & Cytochemistry 45(3) : 327 (Year: 1997).*
Summergill et al. Nature Protocols 3 (2) : 220 (Year: 2008).*
Blumentals et al., Characterization of Sodium Dodecyl Sulfate-Resistant Proteolytic Activity in the Hyperthermophilic Archaebacterium Pyrococcus furiosus. Applied and Environmental Microbiology 56(7) :1992 (Year: 1990).*
Daniel et al., Thermostable Proteases. Biotechnology and Genetic Engineering Reviews 13:Chapter 3 (Year: 1995).*
de Planell-Saguer et al., Rapid in situ codetection of noncoding RNAs and proteins in cells and formalin-fixed paraffin-embedded tissue sections without protease treatment. Nature Protocols 5 (6) : 1061 (Year: 2010).*
Ebeling et al., Proteinase K from Tritirachium album Limber. Eur. J. of Biochemistry 47 : 91 (Year: 1974).*
Fredricks et al., Paraffin removal from tissue sections from digestion and PCR analysis. Biotechniques (Year: 1999).*
Haki et al., Developments in industrially important thermostable enzymes: a review. Biosource Technology 89:17 (Year: 2003).*
Newton et al., A simplified method for combined immunohistochemistry and in-situ hybridization in fresh-frozen, cryocut mouse brain sections. Brain Research Protocols 9 : 214 (Year: 2002).*

(Continued)

*Primary Examiner* — Ethan C Whisenant
(74) *Attorney, Agent, or Firm* — Patentfile, LLC; Bradley C. Fach; Steven R. Kick (57) ABSTRACT

Disclosed are methods for treating a biological sample for an analyte-staining assay. These methods are conducted with the use of a single aqueous multi-functional composition for the purposes of performing the steps of deparaffinization, rehydration, antigen retrieval and endogenous enzyme blocking simultaneously optionally at an elevated temperature. These methods are alternatively conducted with use of a single aqueous multi-functional composition that contains a thermostable protease for the purpose of deparaffinization, rehydration, antigen retrieval and endogenous enzyme blocking at an elevated temperature.

8 Claims, 3 Drawing Sheets

(56) References Cited

OTHER PUBLICATIONS

Perrin et al., A combined oligonucleotide and protein microarray for the codetection of nucleic acids and antibodies associated with human immunodeficiency virus, hepatitis B virus, and hepatitis C virus infections. Analytical Biochemistry 322 :148 (Year: 2003).*
Rimsza et al., Clinical Microbiology and Infectiouis Disease. 106 :544 (Year: 1996).*
Takami et al., Applied Microbiology and Biotechnology 30 : 120-124 (Year: 1989).*
Kishbaugh et al., Diels-Alder reactions of 2- and 3-nitroindoles. A simple hydroxycarbazole synthesis. Tetrahedron Letters 42 :4783 (Year: 2001).*

* cited by examiner

METHOD OF PRETREATMENT OF BIOLOGICAL SAMPLES FOR AN ANALYTE-STAINING ASSAY METHOD

CROSS-REFERENCE TO RELATED APPLICATION(S)

This application claims the benefit of U.S. provisional patent application Ser. No. 62/250,727, filed Nov. 4, 2015 and entitled "Method of Pretreatment of Biological Samples for Staining". The aforementioned U.S. provisional patent application is herein expressly incorporated by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF INVENTION

The present invention is in the field of biological sample preparation for analyte-staining. The invention includes methods for treatment of biological samples in the forms of tissue or cells for the detection of proteins, biological molecules, cellular components or epigenetic markers.

BACKGROUND

Field of Invention

The invention generally relates to the improvement of the quality of analyte-staining on a biological tissue or cell sample that is affixed onto a solid substrate. More specifically, one or more embodiments of the invention relates to a method of biological sample treatment using a single multi-functional composition to perform multiple steps at an elevated temperature prior to staining of a target to remove paraffin, to rehydrate the deparaffinized sample, to retrieve targets on the sample, and the most importantly, to inhibit endogenous enzymes in the sample that may interfere with the staining. The staining method may be an analyte-staining method whereby an antibody is bound to its target antigen, or by an in situ hybridization method whereby a nucleic acid probe is bound to its target nucleic acid, such as DNA or RNA targets.

Background

Analyte-staining is a technique used to determine the presence of a target that is a protein or an antigen of interest, and to identify the pattern or the quantity of the protein expression in the context of tissue or cell morphology. When the sample source is a tissue sample, the analyte-staining technique is called immunohistochemistry (IHC); when the sample source is from cells, this staining technique is called immunocytochemistry (ICC).

In Situ Hybridization (ISH) is a method to determine the presence of a target that is DNA or RNA of interest, and to identify the pattern or the quantity of the DNA or RNA expression in the context of tissue.

This technology lays on the principle of the utilization of one or more probes that may be antibodies that specifically recognize and bind to the protein of interest, or the utilization of one or more probes that may be nucleotides that specifically recognize and bind to the DNA or RNA of interest. This is well-recognized as the step of "staining". Being well-acknowledged and widely utilized in the field of art, the conventional or standard analyte-staining method is comprised of several preparation steps or pre-treatment steps that are sequentially performed prior to the staining steps.

For the analyte-assays that performed on tissue samples, the sample preparation steps include: 1) fixation of a biological sample, 2) embedding the sample into a matrix such as paraffin to solidify the sample, 3) cutting thin section of sample from the paraffin block and affixing the sections onto a microscope slide, 4) deparaffinization of the sample, 5) rehydration of the sample, 6) target retrieval, and 7) blocking endogenous enzymes present within the sample. Collectively these steps are preparation steps that are performed prior to the actual staining steps in order to prepare the samples for the optimal condition for the consequent staining step. Once the preparation steps have been completed the samples are ready for staining.

Under the situation that the tissue samples are freshly frozen, the above steps are modified accordingly to omit unnecessary steps including steps 2, 4 and 5.

When the sample source is a population of cells, the above steps is typically modified to omit unnecessary steps 2-5.

Formaldehyde-based fixatives are widely-used for fixation of the biological samples. Upon fixation, the aldehyde-based fixatives that have been widely used is generally believed in the field of art to cause cross-link reactions within and between the targets, which strengthen their structure; therefore preserving the morphology and the integrity of the sample. Solidification may further be achieved by freezing or paraffin embedding. The paraffin provides a firm matrix for tissue slicing. It is also considered the best option for long-term preservation of tissue samples.

The presence of paraffin or other equivalent matrix that solidify the sample, however, inhibits the subsequent staining process and results in a poor staining. Therefore, paraffin wax must be completely removed from the sample and the sample must be rehydrated. Deparaffinization is normally performed using organic solvent, such as xylene, toluene, d-limonene or other aliphatic hydrocarbon solvents. Standard histological methods for paraffin removal leave paraffin solvent in the biological sample. The paraffin solvent must be removed and replaced with water (or an aqueous solution) in a process called rehydration. Rehydration restores a sample to a more normal state conducive to molecular analysis.

Typically rehydration is a two-step process. The first step involves removing the paraffin solvent and replacing it with a water-miscible solvent. The ideal solvent for step one is any solvent that is both miscible with the paraffin solvent and with water. Such a solvent would be any alcohol, such as ethanol, methanol, or propanol. Other solvents could include acetone or methylene chloride. The most commonly used alcohol in histological laboratories is ethanol. The samples are incubated through a series of graded solutions starting with a mixture of the alcohol and paraffin solvent, gradually increasing the alcohol concentration until the samples are in pure alcohol. Following completion of this step the paraffin solvent is replaced by an alcohol, such as ethanol.

In the second step the alcohol is removed and replaced with water. The samples are incubated in a series of alcohol and water mixtures, gradually increasing the water concentration until the samples are in pure water. The water (or other aqueous solution) now permeates the sample, thus completing the rehydration process.

As an alternative, recent developments from various investigators have enabled that the deparaffinization be performed with an aqueous solution mixed with media that emulsifies. Upon heating, this aqueous solution would melt the paraffin while allowing the sample to retain in an aqueous environment at all times. Therefore, the next step of rehydration after deparaffinization using an organic solvent in the conventional analyte-staining method can be eliminated.

Paraffin inhibits the staining process, while the fixative solution halts all metabolic activity in the sample and immobilizes the molecular structure by altering their native structure or denaturing their original structure, likely upon creating chemical links within the molecular structure. Such links help maintain the molecular structure during staining and analysis. However such crosslinks may also denature the target by altering the molecular structure in such a way that the probes, antibodies or nucleic acids, can no longer bind to their targeted antigens, proteins, DNA or RNA. In this case the target is referred to as denatured. Denatured targets cannot be recognized by the probes, and the targets must first be retrieved and restored to their native configuration. The process of target retrieval is intended to retrieve targets such that they become recognizable by the probes. This process is alternatively well-recognized as unmasking or epitope unmasking.

There are generally two methods for target retrieval. The first method is termed enzyme antigen retrieval. In this method a proteolytic enzyme is applied to the biological sample and is allowed to moderately digest the protein structures such that the molecular crosslinks that cause target denaturing are broken and the targets are restored to a more natural configuration. The method of enzyme antigen retrieval is poorly understood and it is not clear why this method works for some kinds of targets but not for others. Some examples of proteolytic enzymes that have been shown to work for Enzyme Antigen Retrieval include pepsin, papain, trypsin, Proteinase K, Protease Type XXIV, and chymotrypsin. These enzymes in conventional use have an optimal temperature of 20° C.-37° C. Typically they are used at room temperature without heating. At temperature above 40° C., they lose their enzymatic activity. They are completely non-functional at temperatures of approximately 50° C. or higher. Therefore, when performed the samples are submerged in enzyme solution at a room temperature and allowed to incubate in this solution for about 5-10 minutes. The samples are then rinsed in buffer to complete the enzyme antigen retrieval step.

The second form of target retrieval is typically known as heat-induced antigen retrieval, often also referred to as heat-induced epitope retrieval (HIER). In this method the biological samples are heated to a temperature of about 90° C.-125° C., in an aqueous target retrieval solution. The heating of the sample results in the breaking of the methylene crosslinks caused by the fixation solution, thus restoring the denatured targets to a more natural configuration.

To date, enzyme target retrieval with proteolytic enzymes is rarely performed anymore because it has been shown that heat-induced target retrieval is generally superior. Occasionally the target retrieval is performed sequentially by using both enzyme target retrieval and heat target retrieval sequentially.

Previously it has not been possible to perform both methods of target retrieval simultaneously because the heating step inactivates the enzyme activity before it has had a chance to retrieve the targets.

The last key step prior to probe staining is endogenous enzyme blocking. Frequently the biological samples also contain the same enzymes used in the staining steps as naturally occurring products. Under these circumstances these naturally occurring enzymes are referred to as endogenous enzymes. When biological samples contain these endogenous enzymes, these enzymes must be inactivated prior to staining so that the endogenous enzymes do not interfere with the staining process. The endogenous enzymes that may be relied upon comprise peroxidase and alkaline phosphatase.

Up to date, for the target retrieval procedure, it has not been possible to perform both enzyme antigen retrieval method and heat-induced antigen retrieval method simultaneously because the heating step inactivates the enzyme activity before it has had a chance to retrieve the targets. Furthermore, for blocking, inhibition, or inactivation of an endogenous enzyme, up to date this step has been performed as a unique and individual step and has not been combined with other prior steps when preparing a sample for analyte-staining. Therefore, there is a need for improvement on the currently used analyte-staining methods with fewer steps. A single multi-functional aqueous composition that remains functional at an elevated temperature enables the combination of deparaffinization, rehydration, enzyme target retrieval, heat-induced target retrieval, and endogenous enzyme blocking. It simplifies the current staining assay method to combine multiple key procedures to one single step using one single solution prior to antibody staining, thus minimize possible operation errors either by hand or with automated settings.

SUMMARY

One or more embodiments of the invention relates to a method using a single multiple-functional aqueous composition for the treatment of biological samples for performing a staining assay that enables heating a biological sample to remove paraffin, rehydrating the deparaffinized sample with an aqueous liquid, performing antigen retrieval on the sample to aid in staining quality, and inhibiting endogenous enzymes in the sample that may interfere with staining be performed simultaneous.

There has thus been outlined, rather broadly, some of the features of the invention in order that the detailed description thereof may be better understood, and in order that the present contribution to the art may be better appreciated. There are additional features of the invention that will be described hereinafter.

In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

More details of various aspects of the methods for preparing a biological sample for an immunoassay using a single multifunctional aqueous composition are described below with reference to FIGS. 1-3.

Some embodiments direct a method for treating a biological sample for conducting an analyte-staining assay, which contain sequential steps to obtain a biological sample that is fixed by a fixative and affixed on a solid substrate, to contact the biological sample with one aqueous composition, and to remove the contact from the sample. The aqueous composition comprises a buffered condition and one or more endogeneous enzyme inhibitor. This aqueous composition is capable of hydrating the sample, retrieving the denatured target molecules in the sample that are caused by the fixative, and to inhibit the endogenous enzymes that are naturally occurred in the sample. Upon the removal of the contact from the sample, the treated sample contains an enhanced condition that promotes the recognition and/or quantification of the target molecules when conducting an analyte-assay.

In some embodiments, this method may optionally be performed under an elevated temperature to enhance the intended purposes.

In some embodiments, upon fixation, the samples may be embedded in a matrix that solidifies the sample. Under this condition, the method is performed under a temperature that is at least the melting point of the matrix for a period of time allowing the matrix to melt.

In some embodiments, the aqueous composition may optionally comprise an emulsifying agent that promotes the mixing between a hydrophilic and a hydrophobic material.

In some embodiments, the solid substrate that the sample is affixed upon may be a glass slide, a microtiter well-plate surface, a membrane or a bead.

In some embodiments, the target molecule in the biological sample may be a protein, an antigen, DNA or RNA molecule.

In some embodiments, the endogenous enzyme inhibitor contained in the aqueous composition may be methanol, sodium azide, hydrogen peroxidase, a chelating agent, or any other equivalent material that is capable of inhibiting an endogenous enzyme in the biological sample.

In some embodiments, the endogenous enzymes that commonly occurred in a biological sample may be peroxidase, alkaline phosphatase, or any enzyme that may interfere with the performance of the assay.

In some embodiments, the assay that the treated biological samples are used for may be immunohistochemistry assay, immunocytochemistry assay, in situ hybridization assay, enzyme-linked immunosorbent assay, western-blotting assay, Southern-blotting assay, Northern-blotting assay, or any other assay that follows that principle of utilizing a probe that specifically binds to a particular target of interest in the biological sample.

Some other embodiments direct a method for treating a biological sample for conducting an analyte-staining assay, which contain sequential steps to obtain a biological sample that is fixed by a fixative and affixed on a solid substrate, to contact the biological sample with one aqueous composition, and to remove the contact from the sample. The aqueous composition comprises a buffered condition, one or more protease and one or more endogeneous enzyme inhibitor. This aqueous composition is capable of hydrating the sample, retrieving the denatured target molecules in the sample that are caused by the fixative, and to inhibit the endogenous enzymes that are naturally occurring in the sample. Upon the removal of the contact from the sample, the treated sample contains an enhanced condition that promotes the recognition and/or quantification of the target molecules when conducting an analyte-staining assay.

The presence of the proteases further promotes the digestion of the target in the biological sample, and these proteases are selected from a group of proteases that at an elevated temperature, they remain structurally stable and enzymatically active. The selection for the proteases may be the proteases derived from a thermostable bacteria of the Bacillus genus, Protease S (*Pyrococus furiosus*), Thermitas (*Bacillus cereus*), Thermolysin (*Bacillus thermoproteolyticus*), Proteolysin (*Coprothermobacter proteolyticus*), or any other proteases that may promote the digestion of the target at an elevated temperature in the biological sample.

Some other embodiments direct a method for treating a biological sample for conducting an analyte-staining assay, which contain sequential steps to obtain a biological sample that is fixed by a fixative and affixed on a solid substrate, to contact the biological sample with one aqueous composition, and to remove the contact from the sample. This aqueous composition is capable of hydrating the sample, retrieving the denatured target molecules in the sample that are caused by the fixative, and to inhibit the endogenous enzymes that are naturally occurred in the sample. The aqueous composition is capable of the above-mentioned intended purpose without the addition of any protease or endogenous enzyme inhibitor, yet is capable of inhibiting the endogenous alkaline phosphatase. Upon the removal of the contact from the sample, the treated sample contains an enhanced condition that promotes the recognition and/or quantification of the target molecules when conducting an analyte-staining assay.

BRIEF DESCRIPTION OF THE DRAWINGS

The drawings illustrate the design and utility of various embodiments of the invention. It should be noted that the figures are not drawn to scale and that elements of similar structures or functions are represented by like reference numerals throughout the figures. In order to better appreciate how to obtain the above-recited and other advantages and objects of various embodiments of the invention, a more detailed description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION

Various embodiments are directed to a method for the treatment of a biological sample in a form of a section of tissue or a population of cells in preparation for the detection of the biological analyte within, such as protein, peptide, antigen, or nucleic acid through the specific binding of the biological analyte and a biomarker that specifically binds to the analyte of interest. The tool used for detection the presence, the absence, and/or the amount of the biological analyte is through microscopic analysis. Other objects, features, and advantages of the invention are described in the detailed description, figures, and claims.

Staining is a technique used in microscopic analysis to enhance contrast in the microscopic image. Stains and dyes may be chemical compounds or biological molecules that may optionally tag, conjugated or labeled with chemical compounds. Stains and dyes are often used to highlight structures in biological tissue samples to define and examine particular tissue structure, cell populations, or organelles within individual cells. Stains and dyes may also be specific to particular DNA, proteins, lipids, or carbohydrates to determine the presence or absence, or the quantity of the particular species of interest.

The term "staining" refers to a formation of specific binding interaction between the stains or the dyes to the species of interest. For example, a staining may occur when a biomarker, such as an antibody, specifically binds to a protein or an antigen; when a nucleic acid binds to a DNA or RNA sequence; or when a chemical compound that specifically recognizes the nucleus of a cell and produce visible color upon the subsequent contact of a substrate.

The term "microscopic analysis" refers to techniques that require a microscope, an instrument or a system that are capable of acquiring data and/or images for analysis. It may be a stand-alone bright-field or fluorescent microscope, a cell imager, a spectrometer, a manual or automated slide stainer and scanner, The term "denaturing" refers to a state in which the molecular structure of a protein, DNA or RNA is modified, typically by heat, pH change, alkali, or ultraviolet radiation such that some of their original properties, specific biological activities, or native structures are diminished or destroyed. The native state of a denatured molecule may be retrieved upon the adjustment of pH or the utilization of oxidizing agent.

The techniques that use staining and microscopic analysis comprises (1) methods that use dye or chemicals that targets a particular component of a tissue or a cell to produce differential color visualization; for example, Gram staining, endospore staining, Papanicolaou staining, haematoxylin and eosin (H&E) staining, (2) methods that use antibodies to target specific proteins, such as immunohistochemistry (IHC) or immunocytochemistry (ICC), IHC is used to study tissues whereas ICC is used to study collections of individual cells. The tissue sample may be embedded in a matrix such as paraffin to be solidified, or it may be freshly frozen upon collection. Both of these methods are similar with the main difference being the source of the biological sample, and (3) methods that use a labeled RNA or DNA probe to target a region of mRNA or DNA sequence within a sample, such as in situ hybridization (ISH) or fluorescent in situ hybridization (FISH). ISH or FISH may be performed on a tissue sample or a population of cells. The tissue sample may be embedded in paraffin or it may be freshly frozen upon collection. These different assay methods share similar principles. Embodiments described herein apply to all these techniques and other related techniques that use staining and microscopic analysis.

The procedures of the staining method in the current invention may be modified according to the type of the biological samples tested. Table 1 below presents the key elements of these various staining assays that use different sources of samples.

TABLE 1

Comparison of key steps for variations of staining assay described in the current invention.

| Assay Type | Sample Type | Target Type | Probe Type | Deparaffinization | Rehydration | Endogenous Enzyme Blocking | Heat-Induced Target Retrieval | Thermo stable Enzyme |
|---|---|---|---|---|---|---|---|---|
| IHC | Paraffin-embedded Tissue | Antigen | Antibody | Yes | Yes | Yes | Yes | Yes |
| IHC | Fresh-frozen Tissue | Antigen | Antibody | No | No | Yes | Yes | Yes |
| ICC | Fresh-frozen Cells | Antigen | Antibody | No | No | Yes | Yes | Yes |
| ISH | Paraffin-embedded Tissue | DNA or RNA | Nucleic Acid | Yes | Yes | Yes | Yes | Yes |
| ISH | Fresh-frozen Tissue | DNA or RNA | Nucleic Acids | No | No | Yes | Yes | Yes |
| ISH | Fresh-frozen Cells | DNA or RNA | Nucleic Acid | No | No | Yes | Yes | Yes |

Where certain elements of embodiments may be partially or fully implemented using known components, methods or processes, portions of such known components, methods or processes that are necessary for an understanding of the present invention will be described, and the detailed descriptions of other portions of such known components, methods or processes will be omitted for ease of explanation and to not obscure embodiments of the invention. Further, embodiments encompass present and future known equivalents to the components referred to herein by way of illustration. More details about various processes to implement various embodiments are further described below with reference to FIGS. 1-3.

The analyte-staining method is comprised of several sample preparation and staining steps. In various embodiments, the analyte-staining assay method is described. The described method comprises multiple steps, in which two or more of the individual steps may optionally be performed simultaneously with one single multiple-functional reagent to simplify the method allowing a shorter assay time and minimizing possible operation errors.

Figure 1:
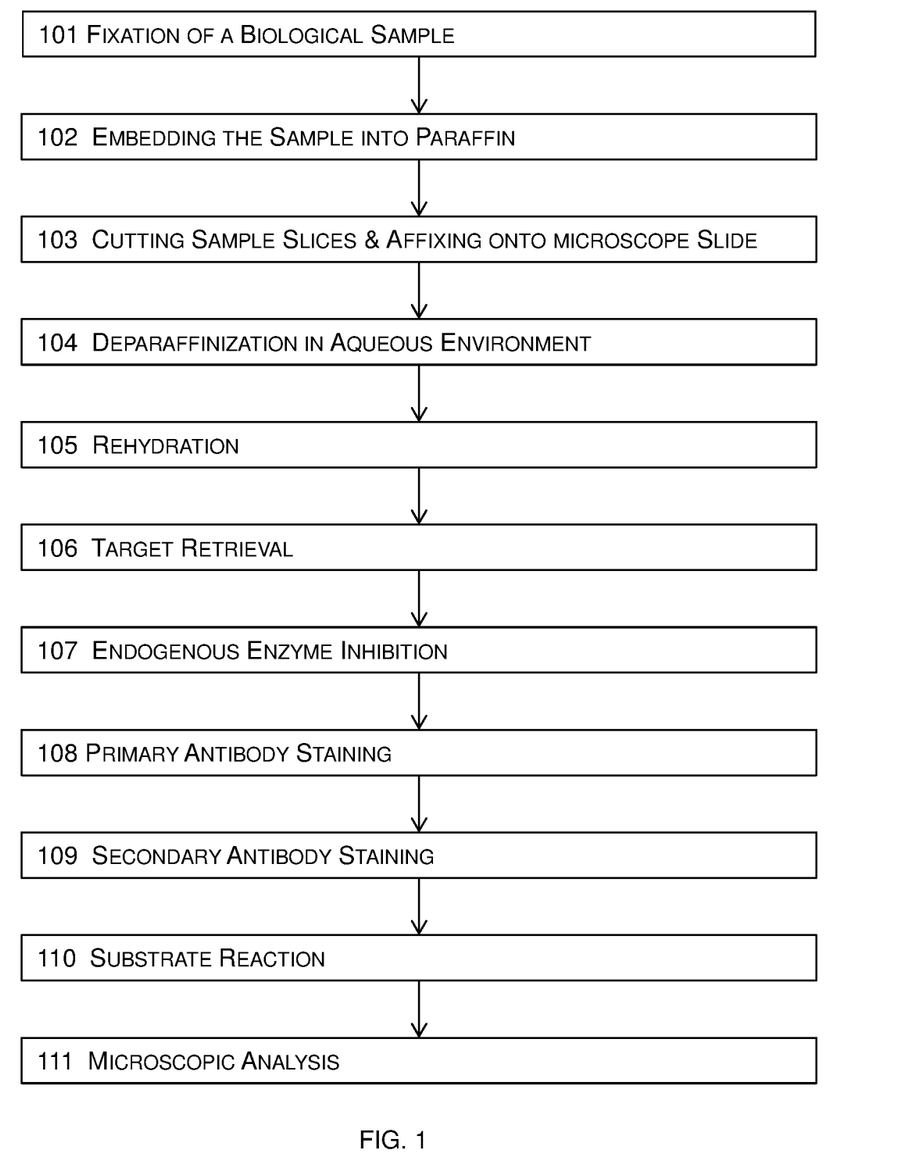
FIG. 1 illustrates a high level block diagram to describe key procedures contained in an analyte-staining assay method.

As illustrated in FIG. 1, the first set of steps comprise preparing a biological sample by: 1) fixing the sample (101), 2) optionally embedding the sample into a solidifying matrix such as paraffin (102), 3) cutting thin section of sample from the paraffin block and affixing the sections onto a microscope slide (103).

The second set of steps comprises preparing a biological sample further by: 4) optionally deparaffinization (104) if step 102 is performed, 5) rehydration (105), 6) target retrieval (106) and 7) inhibition of endogenous enzymes present within the sample (107). Collectively these steps are preparation steps that are performed prior to the actual staining steps. These steps may optionally be performed simultaneously using a single multi-functional composition. Once the preparation steps have been completed the samples are ready for staining.

Once the preparation steps 1) to 7) are completed, the sample is ready for staining which follows the third sets of steps comprising: 8) application of the primary probe which will bind to a target of interest if present in the sample (108), 9) application of a secondary probe that binds to the primary probe and contains an enzyme (109), 10) application of a substrate to the enzyme of step 9 that generates an insoluble color when reacted with the enzyme (110), and 11) preparation of the sample for microscopic analysis to qualify any color reaction that has occurred on the sample (111), and to score or to quantify the amount of the antigen based on the intensity of the color. A positive color reaction indicates that the entire staining sequence has completed satisfactorily, and a positive reaction is indicative that the target of interest is in fact present within the biological sample. Often a scoring system is applied to rank the relative amount of the target present in the sample.

Figure 2:
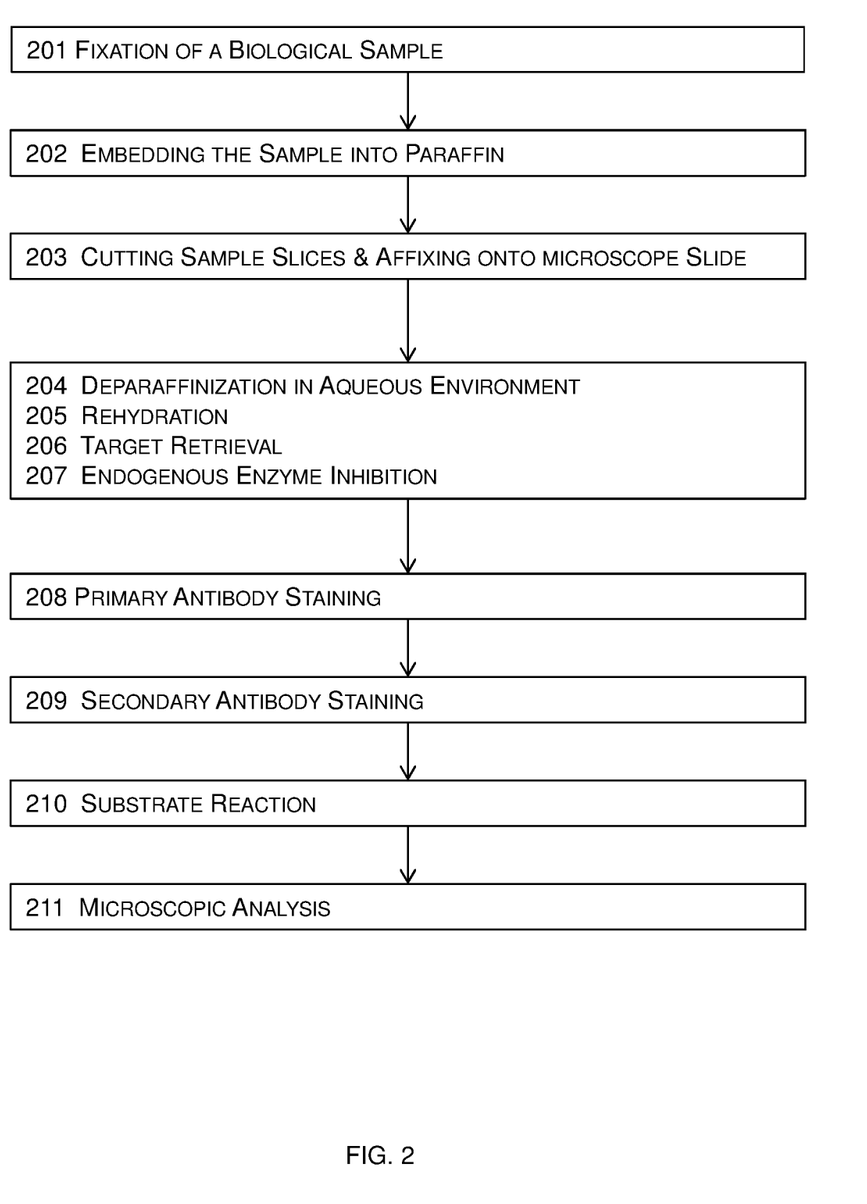
FIG. 2 illustrates a high level block diagram for performing an analyte-staining method in one or more embodiments, in which deparaffinization, rehydration, target retrieval and endogenous enzyme inhibition are performed simultaneously.

In various embodiments, a single aqueous solution is used to perform steps 4)-7) simultaneous with heating, as illustrated in FIG. 2, in which steps 204-207 are treated as one single step. The composition of this multi-functional solution and the heating temperature are optimized for paraffin removal, rehydration, target retrieval and endogenous enzyme inhibition for the desired performance based on the type of biological samples tested.

Figure 3:
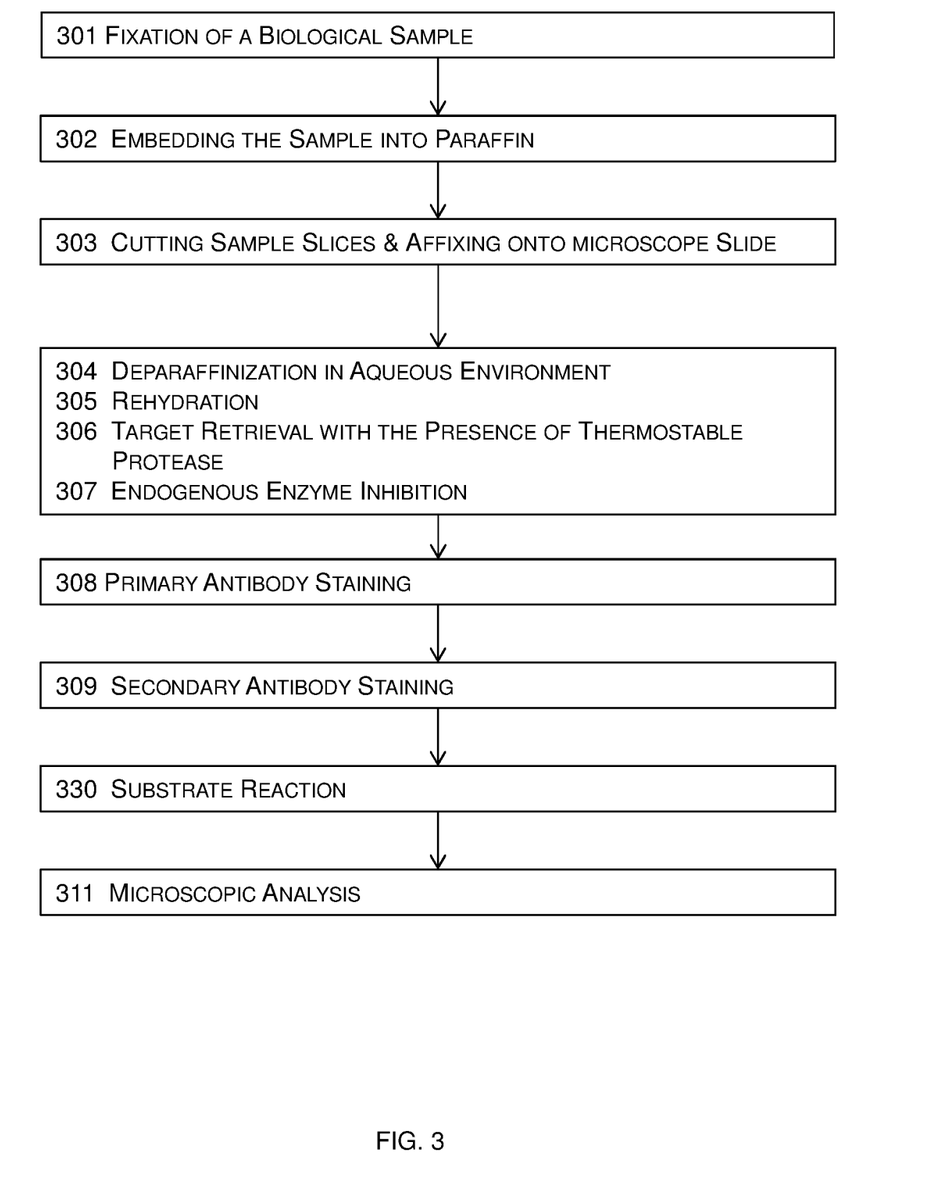
FIG. 3. Illustrates a high level block diagram for performing an analyte-staining method in one or more embodiments, in which deparaffinization, rehydration, target retrieval and endogenous enzyme inhibition are performed simultaneously with the presence of a thermostable protease.

In various embodiments, a single aqueous solution further comprises one or more thermostable protease is used to perform steps 4)-7) simultaneous with heating, as illustrated in FIG. 3, in which step 306 describes target retrieval with the presence of thermostable protease, and steps 304-307 are treated as one single step. The composition of this multi-functional solution and the heating temperature are optimized for paraffin removal, rehydration, target retrieval and endogenous enzyme inhibition for the desired performance based on the type of biological samples tested.

The key elements of the multi-functional solution comprises (1) an aqueous buffer solution, (2) one or more detergents, surface-active agents, emulsifying agents, or surfactants that help disperse the melted paraffin into the aqueous solution and promote target retrieval, (3) a thermostable proteolytic enzyme that remains active at temperature at least higher than 40° C. and (4) one of more chelating agents that promote target retrieval and also aid in the inhibition of endogenous enzymes.

The multi-functional solution may optionally further comprise materials in additional to the chelating agents that further enhance the inhibition of endogenous enzymes.

The buffer solution controls the pH and provides an isotonic environment for the sample. The composition of buffer and its pH are formulated and optimized for desired assay performance. The buffer solution may be acidic (pH<7) buffer, such as citrate buffer or phosphate buffer. The buffer solution may be basic (pH>7) buffer, such as phosphate, EDTA, Tris-HCl or Tris-EDTA buffer The detergent or the emulsifying agent may be Tween-20®, Tween-80®, and other nonionic surfactant Tween family, Triton X-100®, nonionic surfactant Span® family, IGEPAL® polymer family, Nonidet P-40, CD TAB, and any detergent or surfactant that promote dispersion and interaction of a hydrophobic substance into a hydrophilic environment.

The thermostable proteolytic enzyme aids in target retrieval by using a mechanism completely different from heat-induced target retrieval. Target retrieval by heating unfolds the targets and exposes hidden probe-binding sites. The thermostable proteolytic enzyme partially digests targets thus exposes the hidden probe-binding sites. When the target retrieval reagent containing a thermostable proteolytic enzyme is heated, two different retrieval mechanisms are concurrently employed; thus a synergistic effect is obtained. The thermostable proteolytic enzyme such as Protease S (*Pyrococus furiosus*), Thermitas (*Bacillus cereus*), Thermolysin (*Bacillus thermoproteolyticus*), Proteolysin (*Coprothermobacter proteolyticus*) may be used. Such thermostable enzymes show optimal enzymatic activity at temperatures above 40° C. They begin losing their activity at about 80° C. and by 100° C. they are mostly non-functional. Therefore, in the current procedure, they have an activity window that begins when the retrieval solution reaches about 40° C. and ends when the temperature reaches 100° C. or above.

The chelating agent promotes target retrieval to make the target retrieval process more effective. It also promotes inhibition of endogenous enzymes. The chelating agent may be any chelating agent such as citrate, ethylenediaminetetracetic acid (EDTA) or diethylenetriaminepentaacetic acid (DTPA), citrate.

Additional material may be formulated into the single multi-functional composition for blocking endogenous enzymes. For blocking endogenous peroxidase enzyme, hydrogen peroxide ($H_2O_2$), sodium azide ($NaN_3$), hydroxycarbazole, or methanol (MeOH) may be used. For blocking endogenous alkaline phosphatase, HCl, or the chemical Levamisol may be used. Other chemicals that block endogenous peroxidase may be used provided they do not interfere with the subsequent staining steps of the analyte-staining method. Final concentration of the material may be formulated in order to achieve a desired or optimal assay performance.

The method of heating the biological sample in the single multi-functional solution may be achieved by various heating methods comprising a water bath, a steamer, a microwave oven, a convection oven, a pressure cooker, or an autoclave. Any method of heating the Antigen Retrieval solution to a temperature of approximately 90° C.-125° C. may be used.

In one or more embodiments, a method for treatment of a biological sample for an analyte-assay staining is described with the utilization of single aqueous multi-functional composition to perform simultaneously the steps of deparaffinization, rehydration and target retrieval under an elevated temperature, wherein the target retrieval is promoted with the utilization of a thermostable proteolytic enzyme that endures high temperature.

In one or more embodiments, a method for treatment of a biological sample for an analyte-assay method is described with the utilization of single aqueous multi-functional composition to perform simultaneously the steps of deparaffinization, rehydration, target retrieval and endogenous enzyme blocking, as illustrated in FIG. 2 where steps 204-207 are combined and treated as one single step.

In one or more embodiments, a method for treatment of a biological sample for an analyte-assay method is described with the utilization of single aqueous multi-functional composition to perform simultaneously the steps of deparaffinization, rehydration, target retrieval and endogenous enzyme blocking, wherein the single aqueous multi-functional composition comprises a thermostable protease, as illustrated in FIG. 3 where step 306 comprises a thermostable protease.

In various embodiments, the formulation of elements in the aqueous multi-functional composition may vary allowing optimization of performance based on the type of biological samples tested in an analyte-staining assay method In one or more embodiments, the aqueous multi-functional composition comprises a thermostable proteolytic enzyme that remains functionally active at an elevated temperature for the purpose of target retrieval to enhance the quality of staining in an analyte-staining method.

In one embodiment or in some embodiments, it describes a method for treating a biological sample for an analyte-staining assay that comprises a step of removing of the paraffin that is performed by heating the biological sample in an aqueous solution until the paraffin is melted into a surrounding aqueous solution. The melted paraffin can then be removed by discarding the aqueous solution leaving behind the deparaffinized sample. The process of deparaffinization is frequently carried out on a thin section of the biological sample that has been attached to a microscope slide.

In one embodiment or in some embodiments, it describes a method for treatment of a biological sample that does not require a separate rehydration step because the deparaffinization is conducted in an aqueous environment resulting in the sample being automatically rehydrated as the paraffin is removed.

Various embodiments describe a method for antigen retrieval in an analyte-staining assay, in which both enzyme target retrieval method and heat-induced target retrieval method are used simultaneously. The enzyme used is selected from a group of proteolytic enzymes that have the unique characteristic of heat stability. Whereas most enzymes show optimal activity at 37° C. or lower, there are enzymes that have optimal activity at 40° C. or higher. One such enzyme is protease, isolated from the bacterium *Bacillus licheniformis*.

In one embodiment or in some embodiments, it describes a method of sample preparation for analyte-staining that does not require a separate step for blocking the endogenous enzymes. The single multi-functional retrieval solution described in various embodiments may also contain enzyme inhibitory agents. Upon heating, this solution serves multiple functions for the target retrieval as well as endogenous enzyme blocking/inhibition.

In one embodiment or in some embodiments, it describes a single aqueous solution for treating a biological sample in preparation for analyte-staining used for the purposes of deparaffinization, rehydration, target retrieval and endogenous enzyme inhibition. The aqueous-based solution comprises materials that dissolve the paraffin wax upon heating to the temperature above the melting point of paraffin. The aqueous solution allows for the biological sample being kept in an aqueous environment therefore hydrated. The aqueous-based solution further comprises materials that break up the cross-link within the target upon fixation of the biological sample where the target resides. The aqueous-based solution further comprises materials that inhibit the activity of the endogenous enzymes that may otherwise interfere with the subsequent staining step.

In one or more embodiments, it describes a method for treating a biological samples that is paraffin embedded for an analyte-staining assay. The method uses a single aqueous solution for treating the paraffin embedded tissue sample for the purposes of deparaffinization, rehydration, target retrieval and endogenous enzyme inhibition. The aqueous-based solution comprises materials that dissolve the paraffin wax upon heating to the temperature above the melting point of paraffin. The aqueous solution allows for the biological sample being kept in an aqueous environment therefore hydrated. The aqueous-based solution further comprises materials that break up the cross-link within the target upon fixation of the biological sample where the protein, the DNA or the RNA resides. The aqueous-based solution further comprises materials that inhibit the activity of the endogenous enzymes that may otherwise interfere with the subsequent staining step. It may optionally comprise one or more thermostable enzymes that enhance target retrieval.

In one or more embodiments, it describes a method for treating a biological samples that is a population of cells for an analyte-staining assay. The method uses a single aqueous solution for treating the population of cells for the purposes of target retrieval and endogenous enzyme inhibition. The aqueous-based solution comprises materials that break up the cross-link within the protein, the DNA or the RNA in the cells upon fixation. It further comprises materials that inhibit the activity of the endogenous enzymes that may otherwise interfere with the subsequent staining step. It may optionally comprise one ore more thermostable enzymes that enhances antigen retrieval.

In one or more embodiments, it describes a method for treating a biological samples that is freshly frozen for an analyte-staining assay. The method uses a single aqueous solution for treating the population of cells for the purposes of target retrieval and endogenous enzyme inhibition. The aqueous-based solution comprises materials that break up the cross-link within the protein, the DNA or the RNA in the tissue upon fixation. It further comprises materials that inhibit the activity of the endogenous enzymes that may otherwise interfere with the subsequent staining step. It may optionally comprise one or more thermostable enzymes that enhances antigen retrieval.

Example 1. Testing of Aqueous Multi-Functional Composition for Deparaffinization Various formulations of aqueous multi-functional compositions were tested to demonstrate their capability for deparaffinization.

The selected biological tissue samples were each fixed, embedded into paraffin wax, cut to slices of 4 μm thickness and affixed onto a glass microscope slide. Two kinds of aqueous multi-functional composition (Entries 2-3 on Table 1) were prepared according to the following formulation.

Aqueous Composition A comprises 0.1 M Citrate buffer at pH 6 and 0.1% Tween 20.

Aqueous Composition B comprises 50 mM Tris-EDTA buffer at pH 9 and 0.1% Tween 20.

Six commercially available aqueous reagents were obtained (Conventional Reagents A-F, Entries 4-9 on Table 1) and one commonly used organic-based reagent system was used for comparison (Entry 1 on Table 1) which will be referred to as the reference system.

An example of Conventional Reagent A is Citrate Buffer commercialized from Dako Corp.

An example of Conventional Reagent B is Trilogy Buffer commercialized from Cell Marque Corp.

An example of Conventional Reagent C is Citrate Buffer commercialized from Bio SB Corp.

An example of Conventional Reagent D is High pH Buffer commercialized from Dako Corp.

An example of Conventional Reagent E is DeCloaker Buffer commercialized from BioCare Medical.

An example of Conventional Reagent F is EDTA Buffer commercialized from Bio SB Corp.

The organic-based deparaffinization method served as a reference and contained a series of xylene and alcohol solutions as follows: 1) 100% xylene, 2) 100% xylene, 3) 50% xylene/alcohol mixture, 4) 100% Alcohol, 5) 70% Alcohol in water, 6) 50% Alcohol in water, 7) 100% water. For the reference slides the sliced tissues were exposed sequentially to each reagent for three minutes each. For the aqueous deparaffinization methods, the sliced tissue samples affixed on the glass slides were submerged into each of the deparaffinization reagents.

For the samples submerged in the aqueous solutions, the reagent solution was heated beginning at a temperature of about room temperature, or 22° C. to a final temperature of about 121° C. using a pressure cooker. At a temperature of about 55-65° C. the paraffin was melted and dispersed into the hot aqueous solution. Upon reaching the final temperature of 121° C. the aqueous solution was then discarded while still hot along with the melted paraffin. The slides were removed to a fresh buffer at pH 7.6 that is free of melted paraffin. The slides were additionally rinsed with a new batch of fresh buffer, mounted in an aqueous mounting medium and ready to be scored.

For the reference sample submerged in the organic reagents that contains xylene and alcohol, the sample remain submerged at room temperature without heating. This sample was then removed from the last container of water, mounted in an aqueous mounting medium and ready to be scored.

Deparaffinization was graded visually on a scale of 0 to 4 with 0 representing poor deparaffinization and 4 representing complete deparaffinization. Incomplete deparaffinization may be visualized on the slides as greasy or waxy areas or hydrophobic areas that repel aqueous solution such as those used in subsequent sample preparation and/or staining steps.

Reagent spread was also graded as a measure of the repulsion of aqueous reagents due to remaining paraffin. It was graded on a scale of 0 to 4 with 0 representing poor reagent spread and 4 representing complete and homogenous reagent spread.

Table 1 presents the results of testing of deparaffinization & rehydration effects on the aqueous multi-functional various aqueous and organic reagents.

| | Deparaffinization Reagent | Deparaffinization Score | Reagent Spread Score |
|---|---|---|---|
| 1 | Xylene and alcohol (Reference method, organic based) | 4 | 4 |
| 2 | Aqueous Composition A | 3 | 4 |
| 3 | Aqueous Composition B | 3 | 4 |
| 4 | Conventional Reagent A | 2.5 | 3 |
| 5 | Conventional Reagent B | 3 | 4 |
| 6 | Conventional Reagent C | 2 | 3 |
| 7 | Conventional Reagent D | 3 | 3 |
| 8 | Conventional Reagent E | 3 | 4 |
| 9 | Conventional Reagent F | 2 | 3 |

Example 2. Testing of the Aqueous Multi-Functional Composition for Endogenous Enzyme Inhibition Various formulations of multi-functional composition were tested to demonstrate their capability for endogenous enzyme inhibition.

The biological tissue samples were each fixed, embedded into paraffin wax, cut to slices of 4 μm thickness and affixed onto a glass microscope slide. Two types of basic composition were prepared: citrate buffer based Composition A and tris-EDTA buffer based Composition B. Each of the buffer solutions was further formulated to include various endogenous enzyme inhibitors individually or combined: methanol, hydrogen peroxide, sodium azide.

Aqueous Composition A comprises 0.1 M Citrate buffer at pH 6 and 0.1% Tween 20.

Aqueous Composition B comprises 50 mM Tris-EDTA buffer at pH 9 and 0.1% Tween 20.

Methanol (MeOH) was mixed into either the citrate or Tris-EDTA buffer at a final concentration of 1%.

Hydrogen peroxide ($H_2O_2$) was mixed into either the citrate or Tris-EDTA buffer at a final concentration of 0.01%

Sodium azide ($NaN_3$) was mixed into either the citrate or Tris-EDTA buffer at a final concentration of 0.01%

These buffer solutions containing various inhibitors were used as a single agent for deparaffinization, rehydration, target retrieval and endogenous enzyme inhibition. A pair of two slides with tissue sample affixed was submerged into each buffer solution. The buffer solutions were heated from room temperature (about 22° C.) to a final temperature of 121° C. using a pressure cooker. After reaching a maximum temperature the slides were allowed to cool to about 90° C. before they were removed to a fresh buffer bath. The entire heating and cool cycle lasted about one hour. At temperatures of about 55° C. C.-65° C. the paraffin was melted and dispersed into the aqueous buffer solution. Simultaneously with the removal of the paraffin, the slides were rehydrated from the surrounding buffer solution. At temperatures of about 80° C. C.-121° C. thermal decomposition of hydrogen peroxide occurred with the concomitant inhibition of endogenous peroxidase. At temperatures of about 100° C. C.-121° C., the tissues underwent heat-induced target retrieval. Upon the completion of the incubation, all the slides were processed for staining. To test for any remaining endogenous enzymes the tissues were stained with a substrate for peroxidase comprised of 0.05% Diaminobenzidine plus 0.01% Hydrogen Peroxide in 50 mM Tris Buffer, pH 7.6, or a substrate for Alkaline Phosphatase containing 0.01% Naphthol-Phosphate plus 0.01% Fast Red B in 50 mM Tris buffer at pH 8.3.

The slides were analyzed microscopically for the present of any reaction product. A brown reaction product formed by the interaction of peroxidase with Diaminobenzidine/Hydrogen Peroxide indicated the presence of endogenous peroxidase enzyme. A red reaction product formed by the interaction of alkaline phosphatase with Naphthol-Phosphate/Fast Red B indicated the presence of endogenous alkaline phosphatase. Zero (0) percent inhibition was set as the amount of staining present on the slide that contained no inhibitor. Slides that contained no color were set at 100% inhibition. The amount of inhibition between 0% and 100% were visually estimated based on the amount of color observed on the slides when examined microscopically.

Table 3 presents the results of testing of endogenous enzyme inhibition effects on various buffer solutions.

| | Target Retrieval Buffer Base | Inhibitor | Percent (%) Inhibition | |
|---|---|---|---|---|
| | | | Peroxidase | Alkaline phosphatase |
| 1 | Aqueous Composition A | None | 0% | 100% |
| 2 | Aqueous Composition A | MeOH | 70% | 100% |
| 3 | Aqueous Composition A | $H_2O_2$ | 70% | 100% |
| 4 | Aqueous Composition A | $NaN_3$ | 70% | 100% |
| 5 | Aqueous Composition A | MeOH + $H_2O_2$ | 100% | 100% |
| 6 | Aqueous Composition A | $NaN_3$ + $H_2O_2$ | 100% | 100% |
| 7 | Aqueous Composition B | None | 0% | 100% |
| 8 | Aqueous Composition B | MeOH | 80% | 100% |
| 9 | Aqueous Composition B | $H_2O_2$ | 80% | 100% |
| 10 | Aqueous Composition B | $NaN_3$ | 80% | 100% |
| 11 | Aqueous Composition B | MeOH + $H_2O_2$ | 100% | 100% |
| 12 | Aqueous Composition B | $NaN_3$ + $H_2O_2$ | 100% | 100% |

As can be seen by Table 2, all 12 formulations achieved 100% inhibition of endogenous alkaline phosphatase. The addition of MeOH, $H_2O_2$ or $NaN_3$ may optionally be excluded to still maintain 100% inhibition with only the basic composition alone.

For the inhibition of endogenous peroxidase enzyme, the presence of an inhibitor was required. All formulations except for Inhibitors in the target retrieval buffer (entries 2-6 and 8-12), were successful in achieving a percent inhibition of 70% or higher.

Example 3. Comparison of the Multi-Functional Composition to the Commercially Available Antigen Retrieval Reagents Various formulations of multi-functional composition used in Example 2 were tested and compared with various commercially available antigen retrieval reagents to demonstrate their differences in function.

The biological tissue samples were each fixed, embedded into paraffin wax, cut to slices of 4 μm thickness and affixed onto a glass microscope slide. The two aqueous composition A and B as described in Example 1 were further formulated to generate four formulations of the aqueous multi-functional composition: (1) Citrate buffer containing MeOH and $H_2O_2$, (2) Citrate buffer containing $NaN_3$ and $H_2O_2$, (3) Tris-EDTA buffer containing MeOH and $H_2O_2$, and (4) Tris-EDTA buffer containing $NaN_3$ and $H_2O_2$. In addition, six commercially available antigen retrieval reagents as described in Example 1, Conventional Reagent A-F, were used as listed in Table 4, entries 3-5 and 8-10.

All ten reagents were used as a single reagent for deparaffinization, rehydration, target retrieval and endogenous peroxidase inhibition as described in Example 2.

Upon the completion of the heating and cooling cycle described in Example 2, all the slides were processed for staining. To test for any remaining endogenous peroxidase the tissues were stained with a substrate for peroxidase comprised of 0.05% Diaminobenzidine plus 0.01% Hydrogen Peroxide in 50 mM Tris Buffer, pH 7.6.

The slides were analyzed microscopically for the present of any reaction product. A brown reaction product formed by the interaction of peroxidase with Diaminobenzidine/Hydrogen Peroxide indicated the presence of endogenous peroxidase enzyme. Zero (0) percent inhibition was set as the amount of staining present in the slide that contained no inhibitor. Slides that showed no staining were set at 100% inhibition. The amount of inhibition between 0% and 100% was visually estimated based on the amount of color observed on the slides when examined microscopically.

Table 4 presents the results of testing of endogenous peroxidase inhibition effects on various formulations including six commercially available reagents trial do not contain an enzyme inhibitor.

| | Target Retrieval Buffer Base + Enzyme inhibitors | Percent (%) Inhibition |
|---|---|---|
| 1 | Aqueous Composition A + MeOH + $H_2O_2$ | 100% |
| 2 | Aqueous Composition A + $NaN_3$ + $H_2O_2$ | 100% |
| 3 | Conventional Reagent A | 0% |
| 4 | Conventional Reagent B | 0% |
| 5 | Conventional Reagent C | 0% |
| 6 | Aqueous Composition B + MeOH + $H_2O_2$ | 100% |
| 7 | Aqueous Composition B + $NaN_3$ + $H_2O_2$ | 100% |
| 8 | Conventional Reagent D | 0% |
| 9 | Conventional Reagent E | 0% |
| 10 | Conventional Reagent F | 0% |

The results in Table 4 show that none of the commercially available antigen retrieval reagents was able to perform the endogenous enzyme inhibition. All of them (entries 3-5 and 8-10) showed no inhibition (0%). Therefore, in order to proceed further, a separate step of endogenous enzyme inhibition using a dedicated reagent is necessary. In contrast, the formulation as described in this example and in various embodiments in this invention is multi-functional with which the single composition alone is sufficient to perform at least the target retrieval and the endogenous enzyme blocking simultaneously.

In conclusion, combining the results shown in Tables 2-4, citrate buffer or Tris-EDTA buffer as described in various embodiments with the addition of MeOH, $H_2O_2$ and $NaN_3$ successfully served multiple functions for deparaffinization, rehydration, antigen retrieval and endogenous enzyme inhibition. These reagents provide supreme advantages allowing one to combine the steps of deparaffinization, rehydration, target retrieval and endogenous enzyme inhibition to one single step.

Example 4. Testing of Aqueous Multi-Functional Composition for the Effect of Protease In this example, the effect of protease on target retrieval was tested by comparing the staining scores using the heat-induced target retrieval method with or without the addition of the protease. The objective of this study is to show that the addition of protease to the heat-induced target retrieval enhances the staining.

The biological tissue samples were each fixed, embedded into paraffin wax, cut to slices of 4 μm thickness and affixed onto a glass microscope slide. Four sets of target retrieval reagents were generated by formulating the two aqueous composition A and B as described in Example 1: (1) Citrate buffer-based reagent containing no protease, (2) Citrate buffer-based reagent containing protease, (3) Tris-EDTA buffer-based reagent containing no protease, and (4) Tris-EDTA buffer-based reagent containing protease.

Aqueous Composition A comprises 0.1 M Citrate buffer at pH 6 and 0.1% Tween 20.

Aqueous Composition B comprises 50 mM Tris-EDTA buffer at pH 9 and 0.1% Tween 20.

A thermostable protease isolated from bacteria of the *Bacillus* genus with a specific activity of 2.4 units/gm was diluted into the antigen retrieval solutions at a dilution of 1:1000.

Other types of thermostable proteases such as Protease S (*Pyrococus furiosus*), Thermitas (*Bacillus cereus*), Thermolysin (*Bacillus thermoproteolyticus*), Proteolysin (*Coprothermobacter proteolyticus*) may be used. Due to their similar properties, it is expected that similar results would be obtained.

These buffer solutions were used as a single agent for deparaffinization, rehydration, target retrieval and protease digestion. A pair of two slides with tissue sample affixed was submerged into each buffer solution. The buffer solutions were heated from room temperature (about 22° C.) to a final temperature of 121° C. using a pressure cooker. After reaching a maximum temperature the slides were allowed to cool to about 90° C. before they were removed to a fresh buffer bath. The entire heating and cool cycle lasted about one hour. At temperatures of about 55° C.-65° C. the paraffin is melted and dispersed into the aqueous buffer solution. Simultaneously with the removal of the paraffin, the slides are rehydrated from the surrounding buffer solution. At temperatures of about 60° C.-100° C., the tissues are subjected to protease digestion. At temperatures of about 100° C.-121° C., the tissues undergo heat-induced target retrieval.

Upon the completion of the incubation, all the slides were processed for staining. For each set of 10 slides, ten different primary antibodies were used to each stain one slide. The ten primary antibodies used are: CD20, Ki67, Vimentin, cytokeratin, IgG, estrogen receptor, progesterone receptor, CD7, CD38 and BCL6. These primary antibodies were obtained from Bio SB (Santa Barbara, Calif.) and used without further dilution. Antibodies were incubated on slides for 20 minutes at room temperature, following by three rinses with wash buffer to remove any unbound primary antibody.

Secondary antibody staining was performed using a secondary antibody conjugated with peroxidase that targets the primary antibody. All slides were incubated in the secondary antibody solution for 20 minutes at room temperature. The slides were washed to remove excess and unreacted secondary antibody.

Slides were then stained with a peroxidase substrate comprised of 0.05% Diaminobenzidine plus 0.01% Hydrogen Peroxide for 5 minutes at room temperature.

Slides were evaluated microscopically for the presence or absence of brown reaction product. Slides with no staining received a score of 0, weak staining=2, moderate staining=3, and strong staining=4.

Table 5 presents the results of the impact of adding a proteolytic enzyme antigen retrieval solution.

| Target Retrieval Buffer Base | Proteolytic Enzyme | Primary Antibody | Staining Score |
|---|---|---|---|
| Set 1: Citrate Buffer with No Proteolytic Enzyme. Total Score: 27 | | | |
| Citrate Buffer | — | CD20 | 4 |
| Citrate Buffer | — | Ki67 | 3 |
| Citrate Buffer | — | Vimentin | 3 |
| Citrate Buffer | — | Cytokeratin | 3 |
| Citrate Buffer | — | IgG | 2 |
| Citrate Buffer | — | Estrogen receptor | 3 |
| Citrate Buffer | — | Progesterone receptor | 3 |
| Citrate Buffer | — | CD7 | 2 |
| Citrate Buffer | — | CD38 | 2 |
| Citrate Buffer | — | BCL6 | 2 |
| Set 2: Citrate Buffer with Proteolytic Enzyme. Total Score: 29.5 | | | |
| Citrate Buffer | + | CD20 | 4 |
| Citrate Buffer | + | Ki67 | 3 |
| Citrate Buffer | + | Vimentin | 3.5 |
| Citrate Buffer | + | Cytokeratin | 4 |
| Citrate Buffer | + | IgG | 3 |
| Citrate Buffer | + | Estrogen receptor | 3 |
| Citrate Buffer | + | Progesterone receptor | 3 |
| Citrate Buffer | + | CD7 | 2 |
| Citrate Buffer | + | CD38 | 2 |
| Citrate Buffer | + | BCL6 | 2 |
| Set 3: Tris-EDTA Buffer with No Proteolytic Enzyme. Total Score: 28 | | | |
| Tris-EDTA Buffer | — | CD20 | 4 |
| Tris-EDTA Buffer | — | Ki67 | 3.5 |
| Tris-EDTA Buffer | — | Vimentin | 3 |
| Tris-EDTA Buffer | — | Cytokeratin | 3 |
| Tris-EDTA Buffer | — | IgG | 2.5 |
| Tris-EDTA Buffer | — | Estrogen receptor | 3 |
| Tris-EDTA Buffer | — | Progesterone receptor | 3 |
| Tris-EDTA Buffer | — | CD7 | 2 |
| Tris-EDTA Buffer | — | CD38 | 2 |
| Tris-EDTA Buffer | — | BCL6 | 2 |
| Set 4: Tris-EDTA Buffer with Proteolytic Enzyme. Total Score: 30.5 | | | |
| Tris-EDTA Buffer | + | CD20 | 4 |
| Tris-EDTA Buffer | + | Ki67 | 3.5 |
| Tris-EDTA Buffer | + | Vimentin | 3.5 |
| Tris-EDTA Buffer | + | Cytokeratin | 4 |
| Tris-EDTA Buffer | + | IgG | 3 |
| Tris-EDTA Buffer | + | Estrogen receptor | 3 |
| Tris-EDTA Buffer | + | Progesterone receptor | 3 |
| Tris-EDTA Buffer | + | CD7 | 2 |
| Tris-EDTA Buffer | + | CD38 | 2 |
| Tris-EDTA Buffer | + | BCL6 | 2 |

The data presented in Table 5 show that either the citrate buffer or the Tris-EDTA buffer was capable as a multiple-purpose reagent upon heating. The addition of the proteolytic enzyme at the heated temperature further enhanced the staining. Comparing Set 1 vs. 2, or Set 3 vs. 4, for all 10 different primary antibodies, the total staining score for the set with protease is higher than the set with no protease.

Examples 5. Testing of Protease Effect—Comparison to Commercially Available Antigen Retrieval Reagents The two target retrieval buffer based used in Example 4 with the addition of proteases were further tested in comparison with six other commercially available antigen retrieval reagents (Conventional Reagents A-F as described in Example 1) to show the advantageous staining effect.

The biological tissue samples were each fixed, embedded into paraffin wax, cut to slices of 4 μm thickness and affixed onto a glass microscope slide. Total 8 different antigen retrieval reagents were used as listed in Table 5, where entries 1-2 are the same reagents as used in Set 2 and 4 of Example 4, and entries 3-8 are the same commercially available reagents as used in Examples 1 and 3.

The protease used in this example is derived from a thermostable bacteria of the *Bacillus* genus. Other types of thermostable proteases such as Protease S (*Pyrococus furiosus*), Thermitas (*Bacillus cereus*), Thermolysin (*Bacillus thermoproteolyticus*), Proteolysin (*Coprothermobacter proteolyticus*) may be used. Due to their similar properties, it is expected that similar results would be obtained.

All eight reagents were used as a single reagent for deparaffinization, rehydration, target retrieval and protease digestion. The buffer solutions were heated from room temperature (about 22° C.) to a final temperature of 121° C. using a pressure cooker. After reaching a maximum temperature the slides were allowed to cool to about 90° C. before they were removed to a fresh buffer bath. The entire heating and cool cycle lasted about one hour.

Upon the completion of the incubation, all the slides were processed for staining. For each set of 3 slides, three different primary antibodies (cytokeratin, Vimentin and IgG) were used to each stain one slide at room temperature for 20 minutes. followed by washing for removal of excess and unreacted primary antibodies Secondary antibody staining was performed using a secondary antibody conjugated with peroxidase that targets the primary antibody. All slides were incubated in the secondary antibody solution for 20 minutes at room temperature. The slides were washed to remove excess and unreacted secondary antibody.

The substrate for peroxidase was 0.05% Diaminobenzidine plus 0.01% Hydrogen Peroxide in 50 mM Tris Buffer, pH 7.6 to generate a brown reaction product. The slides were then rinsed and analyzed by microscope. The staining was graded on a scale of 0-4 with 0 representing no staining and 4 representing very strong staining.

Table 6 presents the results of testing of protease effects on various reagents including six commercially available reagents.

|  | Staining Score | | |
| --- | --- | --- | --- |
| Target Retrieval Buffer Formulation | Cytokeratin | Vimentin | IgG |
| 1 Aqueous Composition A + Protease | 4 | 3.5 | 2.5 |
| 2 Aqueous Composition B + Protease | 4 | 4 | 3 |
| 3 Convention Reagent A | 3 | 3 | 2 |
| 4 Convention Reagent B | 3 | 3 | 2 |
| 5 Convention Reagent C | 2.5 | 2.5 | 2 |
| 6 Convention Reagent D | 3 | 3 | 2 |
| 7 Convention Reagent E | 2.5 | 3 | 2 |
| 8 Convention Reagent F | 2.5 | 2.5 | 1.5 |

The results in Table 6 show that with the presence of the protease (entries 1-2), the effect on target retrieval was enhanced, resulting in a higher score of staining compared to the commercially available reagents. Conventional antigen retrieval methods use either heat-induced or enzyme-activated but not combined, due to the fact that the high temperature destroys the enzyme activity. The working example presented here demonstrates that upon the use of a high temperature thermostable proteolytic enzyme, a novel target retrieval method combining both heat and enzymatic activation were achieved to generate advantageous staining results.

Example 6. Testing of Combined Effect of Endogenous Peroxidase Inhibitor and Protease A combined effect of endogenous peroxidase inhibitor and protease was further tested to examine the impact on staining.

The biological tissue samples were each fixed, embedded into paraffin wax, cut to slices of 4 μm thickness and affixed onto a glass microscope slide. The aqueous composition A (Citrate buffer based) and composition B (Tris-EDTA buffer based) were used as the key component with or with no protease and/or the peroxidase inhibitor. Total eight types of antigen retrieval reagents were used as listed in Table 7.

The protease used in this example is derived from a thermostable bacteria of the *Bacillus* genus. Other types of thermostable proteases such as Protease S (*Pyrococus furiosus*), Thermitas (*Bacillus cereus*), Thermolysin (*Bacillus thermoproteolyticus*), Proteolysin (*Coprothermobacter proteolyticus*) may be used. Due to their similar properties, it is expected that similar results would be obtained.

The peroxidase inhibitor used in this example is 0.01% hydrogen peroxide. Other types of peroxidase inhibitors or alkaline phosphatase inhibitors may be used. It is expected that similar results would be obtained.

All eight reagents were used as a single reagent for deparaffinization, rehydration, target retrieval and endogenous enzyme inhibition. One slide with tissue sample affixed was emerged into each reagent. The buffer solutions were heated from room temperature (about 22° C.) to a final temperature of 121° C. using a pressure cooker. After reaching a maximum temperature the slides were allowed to cool to about 90° C. before they were removed to a fresh buffer bath. The entire heating and cool cycle lasted about one hour. At temperatures of about 55° C.-65° C. the paraffin is melted and dispersed into the aqueous buffer solution.

Simultaneously with the removal of the paraffin, the slides are rehydrated from the surrounding buffer solution. At temperatures of about 60° C.-100° C., the tissues are subjected to protease digestion. At temperatures of about 80° C.-121° C. thermal decomposition of hydrogen peroxide occurs with the concomitant inhibition of endogenous peroxidase. At temperatures of about 100° C.-121° C., the tissues undergo heat-induced target retrieval.

Upon the completion of the incubation, all the slides were processed for staining. Primary antibody staining was performed by incubating the slides in cytokeratin antibody solution for 20 minutes at room temperature followed by washing for removal of excessive and unreacted primary antibody.

Secondary antibody staining was performed using a secondary antibody conjugated with peroxidase that targets the primary antibody cytokeratin. All slides were incubated in the secondary antibody solution for 20 minutes at room temperature. The slides were washed to remove excess and unreacted secondary antibody.

The peroxidase substrate comprised of 0.05% Diaminobenzidine plus 0.01% Hydrogen Peroxide in 50 mM Tris Buffer, was reacted with the slides for five minutes at room temperature.

The brown staining for cytokeratin was graded on a scale of 0-4 with 0 representing no staining and 4 representing very strong staining.

The inhibition of endogenous peroxidase enzyme was scored as follows: Zero (0) percent inhibition was set as the amount of staining present in the slide that contained no inhibitor. Slides that showed no staining were set at 100% inhibition. The amount of inhibition between 0% and 100% was visually estimated based on the amount of color observed on the slides when examined microscopically.

Table 7. Combined effect of peroxidase inhibitor and protease in staining score and percentage of inhibition.

| | Target Retrieval Buffer | Staining Score for Cytokeratin | Percent (%) Inhibition of endogenous peroxidase |
|---|---|---|---|
| 1 | Aqueous Composition A | 3 | 0% |
| 2 | Aqueous Composition A + Protease | 4 | 0% |
| 3 | Aqueous Composition A + Peroxidase Inhibitor | 3 | 100% |
| 4 | Aqueous Composition A + Protease + Peroxidase Inhibitor | 4 | 100% |
| 5 | Aqueous Composition B | 3 | 0% |
| 6 | Aqueous Composition B + Protease | 4 | 0% |
| 7 | Aqueous Composition B + Peroxidase Inhibitor | 3 | 100% |
| 8 | Aqueous Composition B + Peroxidase + Peroxidase Inhibitor | 4 | 100% |

The staining score for all 8 reagents shows that when protease was present, a stronger staining was observed that resulted from better target retrieval (score 4 for entries with protease vs. score 3 for without). The inhibition percentage for all 8 reagents shows that a peroxidase inhibitor is needed in order to block the endogenous peroxidase activity (100% for entries with peroxidase inhibitor vs. 0% for without). Overall, for either citrate or Tris-EDTA buffer, buffer alone gave the poorest results for staining (3) and inhibition (0%). In contrast, either buffer containing both the protease and the peroxidase inhibitor generated the best results (score 4 and 100% inhibition).

The results show that the inclusion of both the protease and the peroxidase inhibitor enhances the function of the single reagent such that they are capable of performing multiple functions including deparaffinization, rehydration, antigen retrieval and endogenous enzyme inhibition.

Example 7. Stability of Antigen Retrieval Solutions

The target retrieval solutions used in Examples 1-6 were tested for stability under two reasonable storage conditions: (1) room temperature (15°-25° C.) and (2) refrigerator temperature (4°-8° C.) periodically over the time period of 18 months. Stability studies were conducted by performing the IHC staining on tissue samples using the target retrieval solutions stored at either two storage conditions at the time points selected up to 18 months. The IHC staining procedure is described below.

The biological tissue samples were each fixed, embedded into paraffin wax, cut to slices of 4 μm thickness and affixed onto a glass microscope slide. Citrate buffer and Tris-EDTA buffer were used as the key component with or with no protease and/or the peroxidase inhibitor. Total 14 types of target retrieval reagents were used as listed in Table 8.

The protease used in this example was derived from a thermostable bacteria of the *Bacillus* genus. Other types of proteases may be used. Due to their similar properties, it is expected that similar results would be obtained.

The peroxidase inhibitors used in this example are methanol, sodium azide and hydrogen peroxide. Other types of peroxidase inhibitors or alkaline phosphatase inhibitors may be used. Due to their similar properties, it is expected that similar results would be obtained.

All 14 reagents were used as a single reagent for deparaffinization, rehydration, target retrieval and endogenous enzyme inhibition. One slide with tissue sample affixed was emerged into each reagent heated from room temperature (22° C.) to 121° C. in a pressure cooker as previously described. After reaching the maximum temperature the slides were allowed to cool to 90° C. and then placed into a wash buffer solution. The entire heating and cooling cycle lasted about 60 minutes.

Upon the completion of the incubation all the slides were processed for staining. Each slide was stained with Cytokeratin primary antibody at room temperature for 20 minutes. followed by washing for removal of excess and unreacted primary antibodies Secondary antibody staining was performed using a secondary antibody conjugated with peroxidase that targets the primary antibody. All slides were incubated in the secondary antibody solution for 20 minutes at room temperature. The slides were washed to remove excess and unreacted secondary antibody.

The substrate for peroxidase was 0.05% Diaminobenzidine plus 0.01% Hydrogen Peroxide in 50 mM Tris Buffer, pH 7.6 to generate a brown reaction product. The slides were then rinsed and analyzed by microscope. The staining was graded on a scale of 0-4 with 0 representing no staining and 4 representing very strong staining.

Using the staining results obtained at the starting of the time period ($T_0$) as the reference, the last successful time point which produced comparable IHC staining to $T_0$ is listed in the Table 8. The last time point was conducted at 18 months. The stability was recorded as >18 months if successful staining was achieved at 18 months, Table 8 shows the stability of the target retrieval solutions of the present invention.

| | Target Retrieval Buffer Base | Additive | Longest Stability @ 15°-25° C. | Longest Stability @ 4°-8° C. |
|---|---|---|---|---|
| 1 | Aqueous Composition A | None | >18 months | >18 months |
| 2 | Aqueous Composition A | Methanol | >18 months | >18 months |
| 3 | Aqueous Composition A | Sodium Azide | >18 months | >18 months |
| 4 | Aqueous Composition A | $H_2O_2$ | >18 months | >18 months |
| 5 | Aqueous Composition A | Protease | >12 months | >12 months |
| 6 | Aqueous Composition A | $H_2O_2$ + Protease | 3 months | 12 months |
| 7 | Aqueous Composition A | Methanol + Protease | 3 months | 12 months |
| 8 | Aqueous Composition B | None | >18 months | >18 months |
| 9 | Aqueous Composition B | Methanol | >18 months | >18 months |
| 10 | Aqueous Composition B | Sodium Azide | >18 months | >18 months |
| 11 | Aqueous Composition B | $H_2O_2$ | >12 months | >18 months |
| 12 | Aqueous Composition B | Protease | >12 months | >12 months |
| 13 | Aqueous Composition B | $H_2O_2$+ Protease | 3 months | 12 months |
| 14 | Aqueous Composition B | Methanol + Protease | 3 months | 12 months |

The results from Table 8 show that for either the citrate buffer or the Tris-EDTA buffer, when protease is added, it makes the reagents less stable. When protease coexists with either $H_2O_2$ or methanol, it results in an even lower stability.

Methods and formulations described in various embodiments may generally be used to detect targets in a host of experimental schemes for detecting and visualizing a biological or chemical target, including immunohistochemistry (IHC), immunocytochemistry (ICC). They may further be applied to in situ hybridization (ISH), where specific nucleic acids are used to detect DNA or RNA of interest. They may also further be applied to antibody-based staining methods such as ELISA, Southern, Northern, and Western blotting, and others, with which the biological samples are fixed on a solid substrate other than a glass microscope slide such as beads, microtiter plate or membranes. Instruments that are capable of quantifying the staining intensity are used to determine the outcome of the assay.

The invention claimed is:

1. A method for treating a biological sample for conducting an analyte-staining assay, the method comprising:
   obtaining a biological sample, wherein the biological sample is fixed by a fixative and affixed on a solid substrate;
   contacting the biological sample with an aqueous composition, wherein the aqueous composition comprises as part of its composition; a buffered condition, a proteolytic enzyme, hydroxycarbazole serving as an endogenous peroxidase enzyme inhibitor; and wherein the aqueous composition simultaneously (i) hydrates the sample, (ii) retrieves a denatured target molecule in the biological sample caused by the fixative using the proteolytic enzyme, and (iii) inhibits endogenous peroxidase enzymes with the hydroxycarbazole; and
   heating the biological sample to a temperature greater than 40 degrees C. to trigger heat-induced epitope retrieval (HIER).

2. The method of claim 1, wherein the biological sample is a tissue sample.

3. The method of claim 2, further comprises contacting the biological sample and the aqueous composition under an elevated temperature for a period of time, wherein the temperature is at least a melting point a paraffin of matrix, and the period of time is at least a time that is sufficient for the paraffin matrix to melt.

4. The method of claim 1, wherein the solid substrate is selected from one of; a glass slide, a microtiter well-plate surface, a membrane, and a bead.

5. The method of claim 1, where in the aqueous composition further comprises an emulsifying agent to promote the mixing between a hydrophilic and a hydrophobic materials.

6. The method of claim 1, wherein the solution is heated to a temperature greater than 80 degrees C. to promote heat-induced epitope retrieval (HIER).

7. The method of claim 1, further comprising a solution comprising hydrogen peroxide.

8. The method of claim 1, wherein the proteolytic enzyme is derived from one of a thermostable bacteria of the *Bacillus* genus, Protease S (*Pyrococus furiosus*), Thermitas (*Bacillus cereus*), Thermolysin (*Bacillus thermoproteolyticus*), and Proteolysin (*Coprothermobacter proteolyticus*).

* * * * *